United States Patent [19]

Sharrow et al.

[11] Patent Number: 4,781,681

[45] Date of Patent: Nov. 1, 1988

[54] INFLATABLE TIP FOR LASER CATHETERIZATION

[75] Inventors: James S. Sharrow; Leonard A. Nordstrom, both of Bloomington, Minn.

[73] Assignee: GV Medical, Inc., Minneapolis, Minn.

[21] Appl. No.: 96,926

[22] Filed: Sep. 15, 1987

[51] Int. Cl.$^4$ .............................................. A61M 25/00
[52] U.S. Cl. ..................... 604/96; 604/103; 604/280; 128/658; 128/344; 128/303.1
[58] Field of Search ................................ 128/656-698, 128/633-634, 637, 664-667, 748, 673-675, 772, 303.1, 344; 604/95-103, 280

[56] References Cited

U.S. PATENT DOCUMENTS

| | | | |
|---|---|---|---|
| 4,213,461 | 7/1980 | Pevsner | 128/656 X |
| 4,582,181 | 4/1986 | Samson | 604/95 X |
| 4,592,353 | 6/1986 | Daikuzono | 128/303.1 |
| 4,669,465 | 6/1987 | Moore et al. | 128/303.1 |
| 4,737,145 | 4/1988 | Sharrow | 604/53 X |

*Primary Examiner*—Kyle L. Howell
*Assistant Examiner*—Angela D. Sykes
*Attorney, Agent, or Firm*—Orrin M. Haugen; Thomas J. Nikolai; Frederick W. Niebuhr

[57] ABSTRACT

A transluminal balloon laser catheter has an inflatable distal tip formed by an elongated balloon sealed at the distal end of a length of catheter tubing, and inflatable to an operating configuration in which the balloon effectively extends the distal end of an optical fiber lumen through the catheter tubing. One embodiment of the balloon is formed with a substantially planar distal face, transverse with respect to the extension of the balloon. In an alternative embodiment, the distal face of the balloon is formed as a truncated cone, converging proximally from a radially outward longitudinal balloon section to a radially inward longitudinal balloon section whereby the distal tip of an optical fiber, even when advanced distally of the optical fiber lumen, is proximal with respect to the most distal portion of the balloon.

19 Claims, 2 Drawing Sheets

INFLATABLE TIP FOR LASER CATHETERIZATION

BACKGROUND OF THE INVENTION

This invention relates to catheters, and more particularly to percutaneous transluminal laser catheters.

The use of angioplasty catheters for treating occlusions in blood vessels, particularly in arteries, is well known. Typically such a catheter is equipped with an inflatable balloon near its distal or forward tip. A more recent technique involves providing an optical fiber in the catheter, and extending the distal end of the fiber slightly beyond the distal tip of the catheter, whereby laser energy generated at the proximal end of the fiber is transmitted to an occlusion to be treated. For a further explanation of this technique, reference is made to U.S. patent application Ser. No. 679,633, filed Dec. 10, 1984, now U.S. Pat. No. 4,669,465 and U.S. patent application Ser. No. 887,196, filed July 12, 1986, sending both assigned to the assignee of this application. The proper positioning and orientation of the catheter distal tip is vital to the success of this technique. Precise positioning is essential to ensure that laser energy from the optical fiber is directed onto the occlusion rather than onto the arterial wall. Improper aiming can lead to damage of the wall or, in severe cases, rupture the artery.

Apparatus for positioning a catheter distal tip is known, although not necessarily in connection with transmission of laser energy in a catheter. For example, U.S. Pat. No. 4,582,181 to Samson granted Apr. 15, 1986 shows a dilating catheter inserted into a guide catheter. A flexible helical coil at the catheter distal end can be steered using a knob at the catheter proximal end. Once the catheter is positioned, a balloon near its distal tip is inflated. U.S. patent application Ser. No. 041,996, filed Apr. 24, 1987, pending and assigned to the present assignee, describes a catheter balloon having a blunt forward end particularly well suited for centering the distal tip of a catheter tube.

Further patents disclose placement of an inflatable balloon at or beyond the distal end of the catheter tubing, although not in connection with a laser enhanced angioplasty catheter. For example, U.S. Pat. No. 4,531,943 to Van Tassel et al discloses an inflatable, non-distensible balloon forming a somewhat toroidal distal tip when inflated. The catheter includes a central lumen for supplying fluids to an opening formed by the balloon. A separate balloon inflation lumen is provided to inflate the balloon. U.S. Pat. No. 4,029,104 to Kerber discloses a calibrated leak balloon catheter, in which a balloon is fastened to the outside distal end region of a catheter tube. A discharge orifice is provided through a plug mounted at the distal end of the balloon. While the devices disclosed in these two patents are suitable for particular purposes, they fall short of the need for precise catheter tip positioning in laser enhanced catheters.

Therefore, it is an object of the present invention to provide a means for accurately setting the position and orientation of the distal end of a laser catheter when it is inserted into an artery or other vessel.

Another object of the invention is to provide an inflatable tip for a laser catheter, which tip is particularly well adapted for centering and aiming an optical fiber housed in the catheter.

Yet another object of the invention is to provide improved centering accuracy in a transluminal laser catheter by minimizing the axial extension of the optical fiber distally of the catheter tip feature which locates the optical fiber lumen with respect to the artery being treated.

SUMMARY OF THE INVENTION

To achieve these and other objects, there is provided a laser enhanced transluminal catheter. The catheter includes a length of catheter tubing insertable by its forward end into an artery, and means forming an optical fiber lumen and a balloon inflation lumen in said catheter tubing and extended substantially from its proximal end to its distal end. An optical fiber is contained in the first lumen for transmitting laser energy from the proximal end of the catheter tubing to the distal end. A pliable balloon member is mounted at the distal end of the tubing and cooperates with the tubing to form an inflatable enclosure in fluid communication with the balloon inflation lumen. The enclosure assumes a generally toroidal configuration responsive to a fluid supplied under pressure through the balloon inflation lumen. When inflated, the enclosure includes an annular, longitudinally directed radially inward first section defining a distal end region of the optical fiber lumen; an annular, longitudinally directed second section radially outward of the first section and engaged with a segment of the artery to align the enclosure and arterial segment on a central axis; and a connecting means between the first and second sections for maintaining the first section substantially centered on the central axis. The connecting means includes an annular distal face section of the balloon, which is positioned distally with respect to the distal tip of the catheter tubing.

The distal face can lie substantially in a transverse plane, which tends to longitudinally align the distal ends of the first and second sections. This more precisely controls the orientation of the optical fiber lumen and optical fiber with respect to the second section and arterial segment, as compared to designs in which the catheter tubing tip extends distally of shape of a proximally converging, truncated cone. Preferably the included angle of the cone is greater than the included angle of the laser energy emitted from the optical fiber. This "negative cone" structure places the distal edge of the radially outward second section ahead of the distal end of the optical fiber lumen, permitting placement of the former directly against the occlusion and effectively bringing the therapeutic area of the laser energy closer to the distal end of the balloon catheter, by the longitudinal dimension of the cone recess.

Whether or not the recessed cone is employed, the balloon design of the present invention enables placement of the catheter distal end adjacent a diseased vessel section intended for laser treatment, rather than spaced apart one millimeter or so from it. This millimeter can be the difference between effective application of laser treatment and the inability to use this technique. The shorter tip permits use of the catheter in vessels with smaller curvature radii, so that certain curved vessels are laser treatable - without the threat of wall damage only with the present invention. Further, even in applications where conventional balloons could have been used, the inflatable enclosures constructed in accordance with the present invention ensure greater centering accuracy or aiming of the laser energy, and permit more flexibility in placement of the laser hot spot.

IN THE DRAWINGS

For a better appreciation of the above and other features and advantages, reference is made to the following detailed description and drawings, in which.

DETAILED DESCRIPTION OF THE PREFERRED EMBODIMENTS

Figure 1:
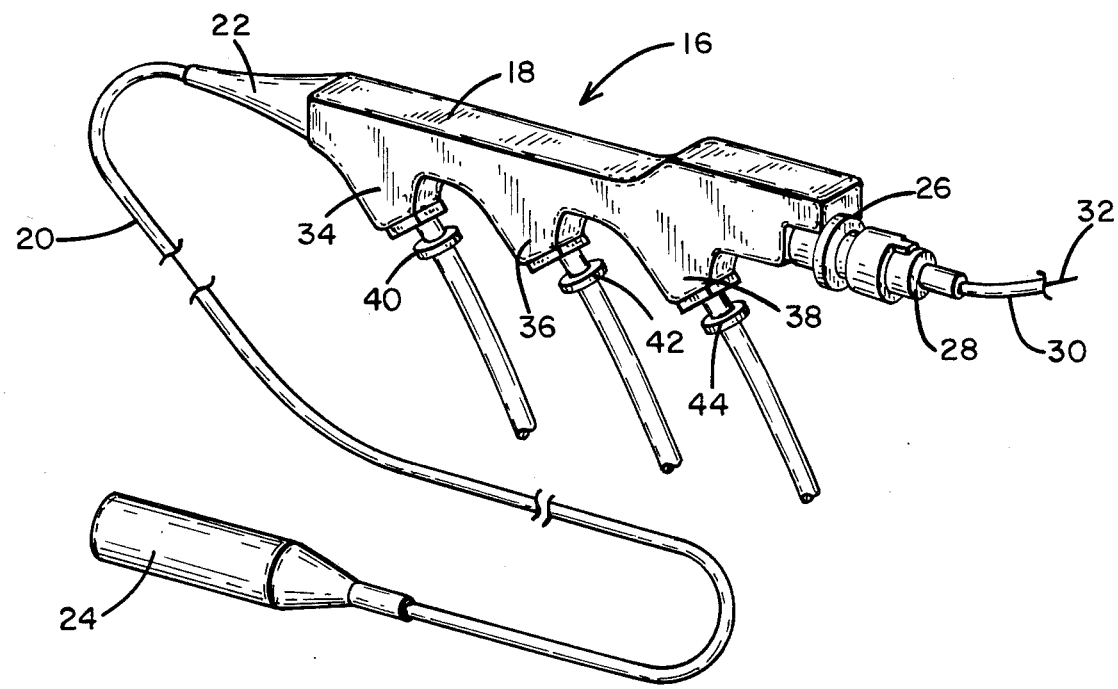
FIG. 1 is a perspective view of a laser enhanced transluminal balloon catheter equipped with an inflatable distal tip in accordance with the present invention.

Turning now to the drawings, there is shown in FIG. 1 a transluminal balloon catheter 16 including a catheter manifold 18 and a length of pliable, polyethylene catheter tubing 20 attached to the catheter manifold and reinforced by a conical strain relief member 22. An elongate catheter balloon 24 surrounds catheter tubing 20 at its distal portion and forms the catheter distal tip.

Joined to the proximal end of manifold 18, through a manifold connector 26 and a sheath connector 28, is an optical fiber sheath 30 containing an optical fiber 32. Sheath 30 is connected at its proximal end to a fiber advance housing which is not illustrated. For more information concerning such fiber advance housing and its relation to the catheter manifold, reference is made to U.S. patent applications Ser. Nos. 679,633 filed Dec. 10, 1984, now U.S. Pat. No. 4,699,465 and 915,507 filed Oct. 6, 1986, sending both assigned to the assignee of this application. Briefly, the fiber advance housing and fiber 32 are moved distally relative to catheter manifold 18 and sheath 30 to advance optical fiber 32 into catheter tubing 20, eventually to a point near the catheter distal tip.

Figure 2:
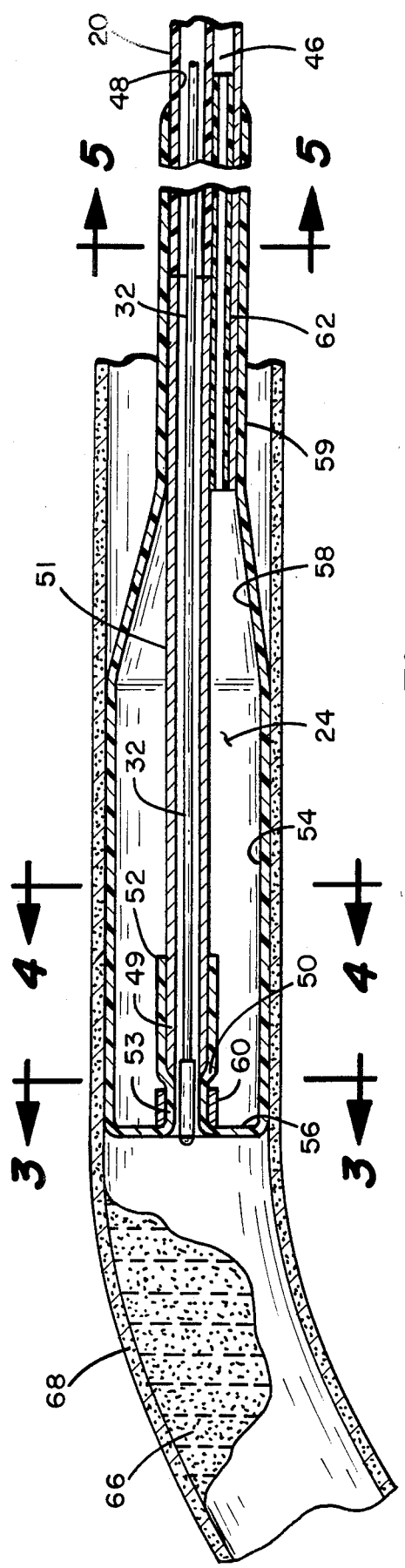
FIG. 2 is an enlarged side sectional view of the distal tip shown in FIG. 1, inflated and positioned within an artery.

Catheter manifold 18 includes first, second and third extensions 34, 36 and 38, to which are connected first, second and third luer fittings 40, 42 and 44. First luer fitting 40 provides fluid under pressure to a balloon inflation lumen 46 (FIG. 2) running through catheter tubing 20 and open to the interior of balloon 24, thus to control dilation and deflation of the distal tip. Second and third luer fittings 42 and 44 deliver treatment fluids, as required, to a central optical fiber lumen 48 also running through the catheter tubing and open to a distal end 49 of the catheter (FIG. 2).

With reference to FIGS. 2-5, balloon 24 is constructed of a material which is pliable yet capable of maintaining the integrity of the balloon configuration when under fluid pressure during normal usage, for example polyolefin. Balloon 24 extends along a distal portion 51 of catheter tubing 20, and includes an annular, radially inward and longitudinally directed first section 50. A proximal portion 52 of first section 50 is sealed to catheter tubing 20, while a distal portion 53 comprising the remainder of the first section extends distally of tubing distal end 49, effectively extending optical fiber lumen 48.

An annular second longitudinal balloon section 54 lies concentric on and radially outwardly of first balloon section 50 when the balloon is inflated. An annular, generally planar distal face section 56 of the balloon joins the distal ends of first and second sections 50 and 54. A gradually tapered section 58 converges proximally from second longitudinal section 54 to an end mounting section or neck 59 sealed to the outside surface of catheter tubing 20. Face section 56 and tapered section 58 cooperate to provide a connecting structure which locates first and second sections 50 and 54 concentric to one another when the balloon is inflated.

Figure 3:
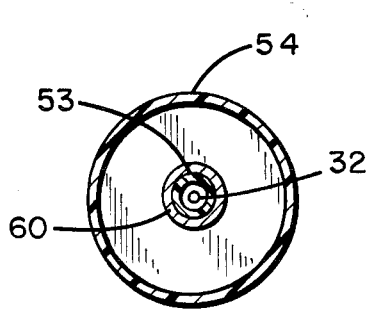
FIG. 3 is a sectional view taken along the line 3—3 in FIG. 2 showing just the tip, inflated.
Figure 4:
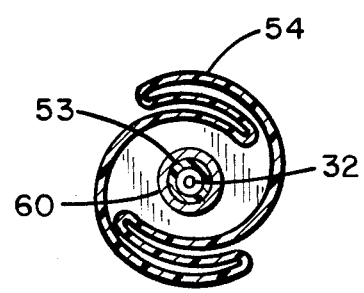
FIG. 4 is a sectional view taken along the line 3—3 in FIG. 2, showing just the tip, deflated.

FIGS. 3 and 4 illustrate balloon 24 in the inflated and deflated conditions, respectively. A distal tip marker 60 is formed of an endless band of radiopaque (radio opaque) material such as platinum or gold, and is mounted around the distal end of first section 50. When the catheter is inserted into an artery, tip marker 60 provides a visual indication of the position of the catheter distal tip.

Figure 5:
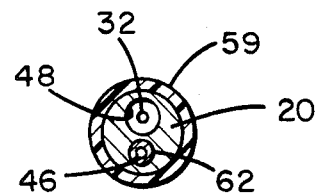
FIG. 5 is a sectional view taken along the line 5—5 in FIG. 2.

As seen from FIG. 5, optical fiber lumen 48 and balloon inflation lumen 46 are both generally circular, with the balloon inflation lumen being somewhat smaller. An elongate, annular sleeve 62 is contained within balloon inflation lumen 46, particularly along the distal end of catheter tubing 20 at the balloon/tube seal zone. Sleeve 62 is formed of a polyimide resin and facilitates manufacture of catheter 16, in that it maintains the configuration of lumen 46 while neck 59 and catheter tubing 20 are subjected to sealing or fusion bonding. A mandrel, not shown, is temporarily inserted into optical fiber lumen 48 along the sealing zone and serves the same purpose as sleeve 62, and is removed after bonding.

Returning to FIG. 2, catheter tubing 20 and balloon 24 are shown contained within a generally cylindrical artery 64. A partial occlusion or blockage 66 is formed in artery 64, and the catheter has been inserted into the artery to remove the occlusion in accordance with a procedure to be described. It should be noted that balloon 24 can be used in curved as well as straight arterial segments, because of the blunt, inflatable distal tip which allows positioning adjacent an occlusion to be treated.

In utilizing catheters in a treatment procedure, the first step is the removal of air from balloon 24 and inflation lumen 46, so that the balloon tends to assume the collapsed shape illustrated in FIG. 4. Also, a "contrast medium" is introduced into artery 68 to map the artery, thus to accurately locate occlusion 66 so that the appropriate balloon diameter may be selected.

The selected catheter tubing then is introduced percutaneously into artery 68, and moved along the artery until the distal region of the catheter is in a predetermined treatment position corresponding to that shown in FIG. 2. The introduction and positioning is accomplished by using a guide wire through lumen 48 as explained in U.S. patent application Ser. No. 916,238, filed Oct. 7, 1986, now U.S. Pat. No. 4,737,145 and assigned to the present assignee. Following positioning, the guide wire is withdrawn and optical fiber 32 is inserted through optical fiber lumen 48 until its distal end is at least near the distal end of lumen 48. All the while, suction is maintained at balloon inflation lumen 46 to maintain the balloon in its collapsed shape.

Following optical fiber insertion, fluid under pressure is introduced to balloon inflation lumen 46 in order to inflate the balloon into an operating configuration as shown in FIGS. 2 and 3. This causes balloon 24 to engage an arterial wall segment 68 along second longitudinal balloon section 54, thus to coaxially position and align balloon 24 and the segment of artery 68 contiguous with the balloon. Following inflation of balloon 24, optical fiber 32 is advanced so that its distal end extends a predetermined distance beyond the balloon distal tip. Then, laser energy is generated at the proximal end of the optical fiber, and transmitted beyond the optical fiber distal end to treat the occlusion.

For convenience and clarity in illustrating optical fiber 32, the fiber is shown with an outside diameter substantially less than the inside diameter of optical fiber lumen 48. However, the preferred outside diameter of the optical fiber, particularly at its distal end, is slightly less than the optical fiber lumen inside diameter. Consequently, optical fiber 32 is free to slide longitudinally with respect to catheter tubing 20 and permits fluid flow around it. At the same time, optical fiber lumen 48 constrains optical fiber 32 against axial movement relative to the tubing, and proper aiming of optical fiber 32 is essentially a matter of accurately centering distal portion 53 of first section 50 within artery 68.

A feature of the present invention resides in the generally transverse orientation of face section 56, and the distal extension of balloon 24 beyond the distal end of catheter tubing 20. First, this arrangement substantially axially aligns the distal end of the optical fiber lumen with the distal end of the balloon feature that aligns the balloon within artery 68, namely second balloon section 54. The effectiveness of second section 54 and face section 56 to control the position of first longitudinal section 50 is enhanced, because of the minimal longitudinal separation.

Secondly, as seen from FIG. 2, this arrangement permits balloon 24 to be positioned extremely close to occlusion 66. By contrast, a catheter in which a portion of the catheter tubing extends distally beyond the balloon cannot be positioned as close to the occlusion. The positioning difference is not large, perhaps on the order of one millimeter. However, in some applications this difference is critical, in that the procedure can be performed only with a balloon catheter having no distal extensions of the catheter tubing, i.e. with a balloon such as balloon 24.

The above features enhance the utility of catheter 16 in curved arterial segments as well as straight segments. In a straight arterial segment, distal end 49 of the catheter tubing and portion 53 are positioned coaxial to the arterial wall segment. In a curved arterial segment, distal end 49 and portion 53 are positioned parallel to the most distal area of tangency, in this case an annular area, between second section 54 of the balloon and the arterial wall segment.

Figure 6:
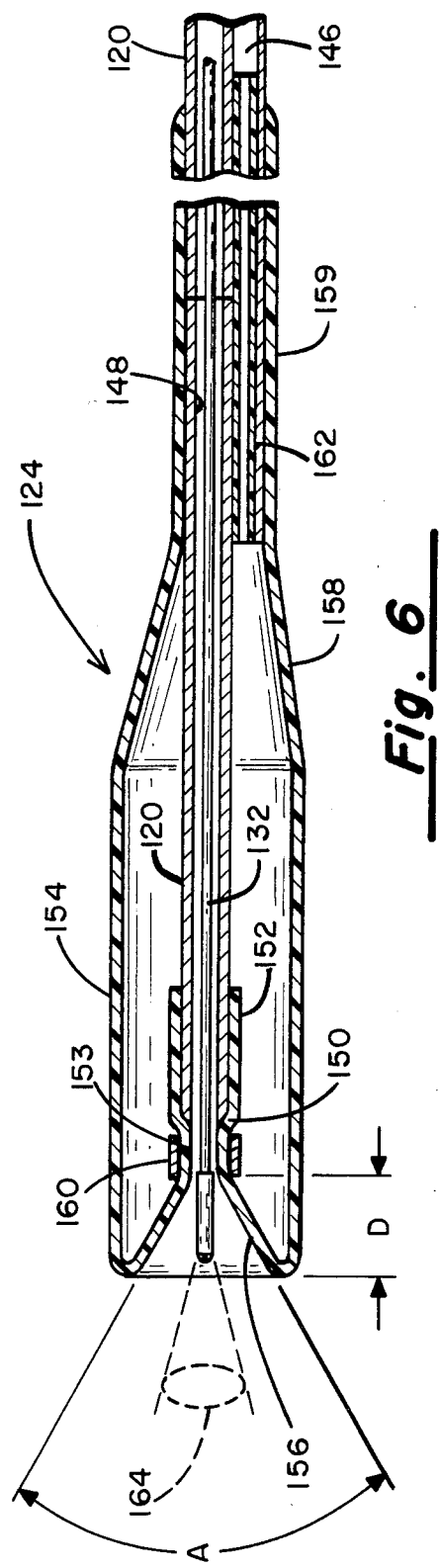
FIG. 6 is a side sectional view of an alternative embodiment inflatable distal tip.

FIG. 6 shows an alternative embodiment catheter having a balloon 124 at the distal end of a length of catheter tubing 120, which is provided with a balloon inflation lumen 146 and an optical fiber lumen 148 containing an optical fiber 132. The tubing, lumens and optical fiber are substantially identical to their counterparts described in connection with catheter 16. Catheter balloon 124 includes a radially inward first section 150 with a distal neck 152 surrounding and sealed to the distal end of catheter tubing 120. An annular inner longitudinal portion 153 of first section 150 extends beyond the tubing distal end and effectively extends optical fiber lumen 148. Concentric with and radially outward of first section 150 is an annular second longitudinal balloon section 154. Connecting outer section 154 and inner section 150 is a conical distal face section 156, shaped like a truncated cone, converging proximally from the distal end of section 154 to the distal end of section 150. Consequently the inner longitudinal section is retracted with respect to the outer section. A tapered section 158 joins outer section 154 with a proximal neck 159, sealed to the catheter tubing. A distal tip radiopaque marker 160 surrounds portion 153 of section 150. A polyimide sleeve 162 is inserted into the balloon inflation lumen along the seal area between proximal neck 159 and the catheter tubing, and performs the same function as sleeve 162.

As seen from FIG. 6, alternative balloon 124 also affords a close positioning advantage, in that the distal end of outer section 154 can be placed directly against the occlusion. Another favorable feature of balloon 124 is that the distal tip of optical fiber lumen 148 is proximal, or recessed, with respect to the distal end of outer section 154. This of course places the inner longitudinal section 150 in direct longitudinal alignment with a portion of outer section 154, ensuring accurate centering of the inner section with respect to the arterial segment.

Further with respect to alternative balloon 124, distal face section 156 is given a selected size and orientation to recess the distal edge of inner section 150 a select distance from the distal edge of outer section 154. For example, in a balloon having an inflated diameter of four millimeters, the included angle of the distal face section (designated A in FIG. 6) is approximately 105°. By contrast, for a balloon with an inflated diameter of two millimeters, the included angle is only 60°. Thus, the distance or longitudinal separation between the distal ends of sections 150 and 154, represented by D in FIG. 6, can remain essentially the same regardless of the balloon size. As a result, the "hot spot" or therapeutic area 164 of laser energy generated near the tip of optical fiber 132 is effectively moved in the proximal direction compared to its position in connection with previously described balloon 24, thus permitting the positioning of this therapeutic area at a selected treatment point closer to the catheter distal tip as determined by the distal edge of section 154. The preferred value for D is one millimeter.

Yet another feature of the truncated cone distal face is that the included angle exceeds the normal included angle of radiated laser energy, which typically is approximately 40°. In the event, however, that laser energy is radiated at an angle offset from the longitudinal axis, distal face section 156 can protect the arterial wall segment against unintentional damage from the laser, particularly if balloon 124 is positioned against an occlusion.

In connection with alternative embodiment balloon 124, it should be noted that the distal tip of optical fiber 132, even though advanced distally beyond optical fiber lumen 148, still lies proximally with respect to the distal end of outer section 154, due to the inverted cone design of the balloon.

An angioplasty catheter equipped with an inflatable tip patterned after either balloon 24 or balloon 124 has increased utility over conventional catheters, particularly in curved arteries. In each design the portion tip which locates the optical fiber is at least substantially longitudinally aligned with the portion of the tip contiguous with the wall of the treated artery. In other words, the distal end of the radially inward balloon section is positioned substantially in longitudinal alignment with, or proximal with respect to, the distal end of the radially outward balloon section. The connecting structure between the radially inward and outward balloon sections, particularly the distal face section, accounts for this positioning, which minimizes the likelihood that any curvature in the treated vessel will adversely affect centering capability.

What is claimed is:

1. A laser enhanced transluminal balloon catheter, including:
    a length of catheter tubing insertable by a distal end thereof into an artery, means forming an optical fiber lumen and a balloon inflation lumen in said catheter tubing, and an optical fiber mounted in said optical fiber lumen, substantially confined axially and slidable longitudinally relative to said catheter tubing, for transmitting laser energy from the proximal end of the catheter tubing to said distal end; and
    a pliable balloon member mounted to said catheter tubing along a tubing distal end portion of the said balloon member and said tubing distal end portion forming a fluid tight enclosure in fluid communication with said balloon inflation lumen, said balloon member including a radially inward first section, a radially outward second section parallel to the tubing distal end portion, and an annular distal face section joining said first and second sections, at least a portion of said first section being contiguous with and sealed to said tubing at least proximate said distal end; and
    wherein said balloon member is inflatable, responsive to a fluid supplied under pressure through said balloon inflation lumen, to an operating configuration wherein said second section is contiguous with a segment of said artery to positively position said enclosure within and relative to said artery, at least a portion of said distal face section is located distally with respect to said distal end, and wherein said distal face section aligns said first section substantially coaxially with said second section.

2. The balloon catheter of claim 1 wherein:
    said first section extends distally beyond said distal end, and said distal face section lies in a substantially transverse plane.

3. The balloon catheter of claim 2 further including:
    an annular radiopaque marker mounted to said first section in surrounding relation thereto and proximate the distal face section.

4. The balloon catheter of claim 1 wherein:
    a portion of said second section extends distally beyond said first section with said balloon member so inflated.

5. The balloon catheter of claim 4 wherein:
    said distal face section comprises a proximally converging truncated cone.

6. The balloon catheter of claim 5 wherein:
    said balloon member further includes a proximal end mounting section sealed against and in surrounding relation to said catheter tubing proximally of said first section, and a proximal wall section gradually converging from said second section to said proximal end mounting section.

7. The balloon catheter of claim 6 further including:
    an elongate, annular sleeve contained in said balloon inflation lumen, a portion of said sleeve being transversely aligned with said proximal end mounting section.

8. The balloon catheter of claim 7 wherein:
    said sleeve is formed of a polyimide resin, and extends beyond the distal end of said balloon inflation lumen into the interior of said enclosure.

9. The balloon catheter of claim 6 further including:
    an annular radiopaque marker mounted to said first section and distally of said catheter tubing.

10. The balloon catheter of claim 5 wherein:
    the included angle of said truncated cone is at least 50°.

11. The balloon catheter of claim 10 wherein:
    said included angle is selected in accordance with the diameter of said second section with said balloon member in said operating configuration, to provide a predetermined longitudinal separation between the distal edges of said first and second sections, thereby to allow the positioning of a therapeutic area of laser energy at a selected treatment location proximate the distal edge of said enclosure.

12. An inflatable tip for a laser enhanced transluminal balloon catheter, wherein the catheter includes a length of catheter tubing insertable by its distal end into an artery, means forming an optical fiber lumen and a balloon inflation lumen in said catheter tubing, and an optical fiber contained in said optical fiber lumen for transmitting laser energy from the proximal end of the catheter tubing to said distal end, said optical fiber further slidable longitudinally and substantially constrained axially with respect to said catheter tubing; said tip including:
    a pliable balloon member mounted to said catheter tubing and extended along a distal portion of said tubing and forming with said distal portion an inflatable, fluid tight enclosure in fluid communication with said balloon inflation lumen;
    said balloon member including a radially inward first section, a radially outward second section parallel to said distal portion, and an annular distal face section joining said first and second sections, with at least a portion of said first section being contiguous with and sealed to said tubing at least proximate said distal end; and
    wherein said balloon member is inflatable, responsive to a fluid supplied under pressure through said balloon inflation lumen, to an operating configuration wherein said second section is contiguous with a wall segment of said artery to positively position said enclosure within and with respect to said artery, at least a portion of said distal face section is located distally with respect to said tubing distal end, and wherein said distal face section aligns said first section substantially coaxially with said second section.

13. The inflatable tip of claim 12 wherein:
    said first section extends distally beyond said distal end, and wherein said distal face section lies in a substantially transverse plane.

14. The inflatable tip of claim 12 wherein:
    a portion of said second section extends distally beyond a distal end of said first section.

15. The inflatable tip of claim 14 wherein:
    said distal face section comprises a proximally converging truncated cone.

16. The balloon catheter of claim 15 wherein:
    the included angle of said truncated cone is at least 50°.

17. The balloon catheter of claim 16 wherein:
    said included angle is selected in accordance with the diameter of said second section with said balloon member in said operating configuration, to provide a predetermined longitudinal separation between the distal edges of said first and second sections, thereby to allow the positioning of a therapeutic area of laser energy at a selected treatment location proximate the distal edge of said enclosure.

18. The inflatable tip of claim 14 wherein:
said balloon member further includes a proximal end mounting section surrounding and sealed against said catheter tubing at a location proximal of said first section, and a proximal wall section gradually converging from said second section to said proximal end mounting section.

19. The inflatable tip of claim 18 further including:
an elongate, annular sleeve contained in said balloon inflation lumen, a portion of said sleeve being transversely aligned with said proximal end mounting section.

* * * * *

UNITED STATES PATENT AND TRADEMARK OFFICE
CERTIFICATE OF CORRECTION

PATENT NO. : 4,781,681

DATED : November 1, 1988

INVENTOR(S) : James S. Sharrow and Leonard A. Nordstrom

It is certified that error appears in the above-identified patent and that said Letters Patent are hereby corrected as shown below:

Column 7, Line 20, "tubing" (second occurrence) should be deleted.

Column 7, Line 20, after "the" insert -- tubing, --.

Signed and Sealed this

Seventh Day of March, 1989

Attest:

DONALD J. QUIGG

*Attesting Officer*   *Commissioner of Patents and Trademarks*